United States Patent
Deason et al.

[19]

[11] Patent Number: 5,822,074
[45] Date of Patent: Oct. 13, 1998

[54] RETROREFLECTIVE SYSTEMS FOR REMOTE READOUT

[75] Inventors: Vance A. Deason; Frederick S. Colwell; Kirk L. Ricks, all of Idaho Falls, Id.

[73] Assignee: Lockheed Martin Idaho Technologies Company, Idaho Falls, Id.

[21] Appl. No.: 804,995

[22] Filed: Feb. 25, 1997

[51] Int. Cl.$^6$ .......................... G01N 21/55; G01K 11/00
[52] U.S. Cl. ........................ 356/445; 356/448; 374/161
[58] Field of Search .................. 374/161, 1, 2; 73/73; 356/445, 446, 73; 356/448

[56] References Cited

U.S. PATENT DOCUMENTS

| | | | |
|---|---|---|---|
| 3,575,515 | 4/1971 | Fertig | 356/199 |
| 3,992,096 | 11/1976 | Oliveira | 356/36 |
| 4,085,314 | 4/1978 | Schultz et al. | 235/487 |
| 4,099,886 | 7/1978 | Oliveira | 356/244 |
| 4,491,923 | 1/1985 | Look | 364/478 |
| 5,260,556 | 11/1993 | Lake et al. | 235/494 |
| 5,444,230 | 8/1995 | Baldwin et al. | 235/462 |
| 5,477,219 | 12/1995 | Zarembo et al. | 340/572 |
| 5,683,180 | 11/1997 | De Lyon et al. | 374/161 |

FOREIGN PATENT DOCUMENTS

| | | | |
|---|---|---|---|
| A2 0 146 522 | 12/1984 | European Pat. Off. | |
| 0014729 | 1/1982 | Japan | |
| WO 82/03914 | 11/1982 | WIPO | |

*Primary Examiner*—Frank G. Font
*Assistant Examiner*—Amanda Merlino
*Attorney, Agent, or Firm*—Thorpe North & Western

[57] ABSTRACT

A sensing device for sensing an environmental factor. The device includes a retroreflective layer disposed in a parallel, facing relationship with a sensing layer. The sensing layer has an initial optical absorption capacity for (i) sensing a presence of an environmental factor, (ii) experiencing a change in optical absorption capacity responsive to said environmental factor, and (iii) transmitting and attenuating light. A first portion of the sensing layer is sealed off from exposure to the environment while a second portion remains exposed to the environment such that, when the environmental factor is present, the first portion of the sensing layer is prevented from experiencing a change in optical absorption capacity responsive to said environmental factor. Well-collimated light beams are passed through the sensing layer and are reflected back from the retroreflective layer for processing. When the environmental factor is present, the beams which pass through the second portion are attenuated responsive to an increase in optical absorption capacity and are compared with the non-attenuated beams passing through the first portion to calculate the presence and quantity of the environmental factor.

12 Claims, 4 Drawing Sheets

RETROREFLECTIVE SYSTEMS FOR REMOTE READOUT

CONTRACTUAL ORIGIN OF THE INVENTION

The United States Government has rights in this invention pursuant to Contract No. DE-AC07-94ID13223 between Lockheed Martin Idaho Technologies Company and The United States Department of Energy.

BACKGROUND OF THE INVENTION

1. Field of the Invention

The present invention relates generally to a device and method for sensing the presence of various factors. More particularly, this invention is directed to constructing a retroreflective assembly having a sensing component of variable optical absorption capacity.

2. Background Art

It is often necessary to sense the presence of, and quantify, various environmental factors such as chemical compounds, temperature, humidity and so forth. Conventional sensors have been developed for this purpose, but have several disadvantages. Many of the conventional sensors of environmental factors require complex electronics for operation, or are not generally remotely readable.

OBJECTS AND SUMMARY OF THE INVENTION

An object of the invention is to provide a sensing device for sensing an environmental factor which is remotely readable by a light source.

Another object of the invention, in accordance with one aspect thereof, is to provide such a sensing device which is operable without utilizing an external power source.

The above objects and others not specifically recited are realized in a specific illustrative embodiment of a sensing device for sensing an environmental factor. The device includes a retroreflective layer disposed in a parallel, facing relationship with a sensing layer. The sensing layer has an initial optical absorption capacity for (i) sensing a presence of an environmental factor, (ii) experiencing a change in optical absorption capacity responsive to said environmental factor, and (iii) transmitting and attenuating light. A first portion of the sensing layer is sealed off from exposure to the environment while a second portion remains exposed to the environment such that, when the environmental factor is present, the first portion of the sensing layer is prevented from experiencing a change in optical absorption capacity responsive to said environmental factor. Well-collimated light beams are passed through the sensing layer and are reflected back from the retroreflective layer for processing. When the environmental factor is present, the beams which pass through the second portion are attenuated responsive to an increase in optical absorption capacity and are compared with the non-attenuated beams passing through the first portion to calculate the presence and quantity of the environmental factor.

Additional objects and advantages of the invention will be set forth in the description which follows, and in part will be apparent from the description, or may be learned by the practice of the invention without undue experimentation. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION OF PRESENTLY PREFERRED EMBODIMENTS

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the illustrated apparatus, and any additional applications of the principles of the invention as illustrated herein, which would normally occur to one skilled in the relevant art and possessed of this disclosure, are to be considered within the scope of the invention claimed.

Applicants have discovered a simple, unique apparatus for sensing the presence and quantity of environmental factors which is remotely readable and which, in some embodiments, does not require an external power source for operation.

Figure 1:
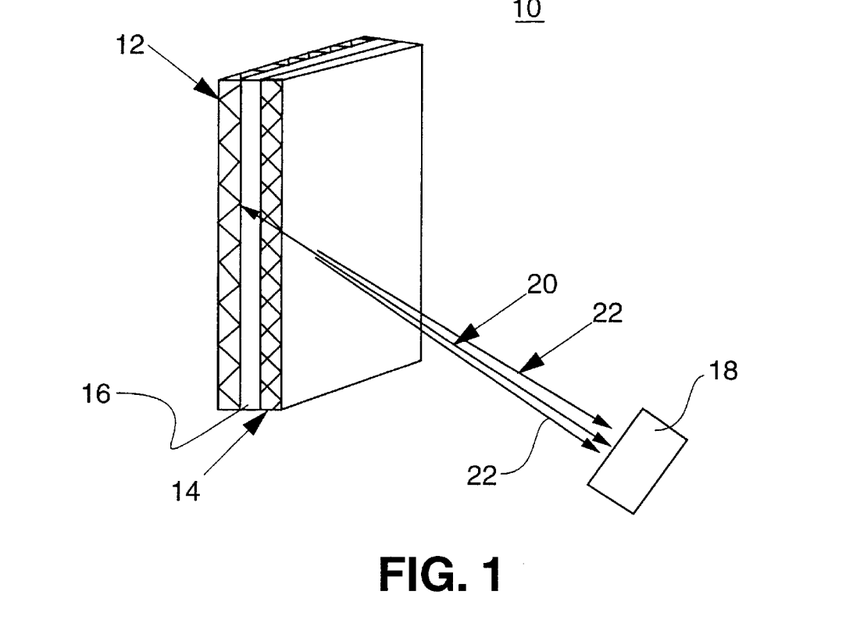
FIG. 1 is a perspective view of a sensing device made in accordance with the principles of the present invention.
Figure 2:
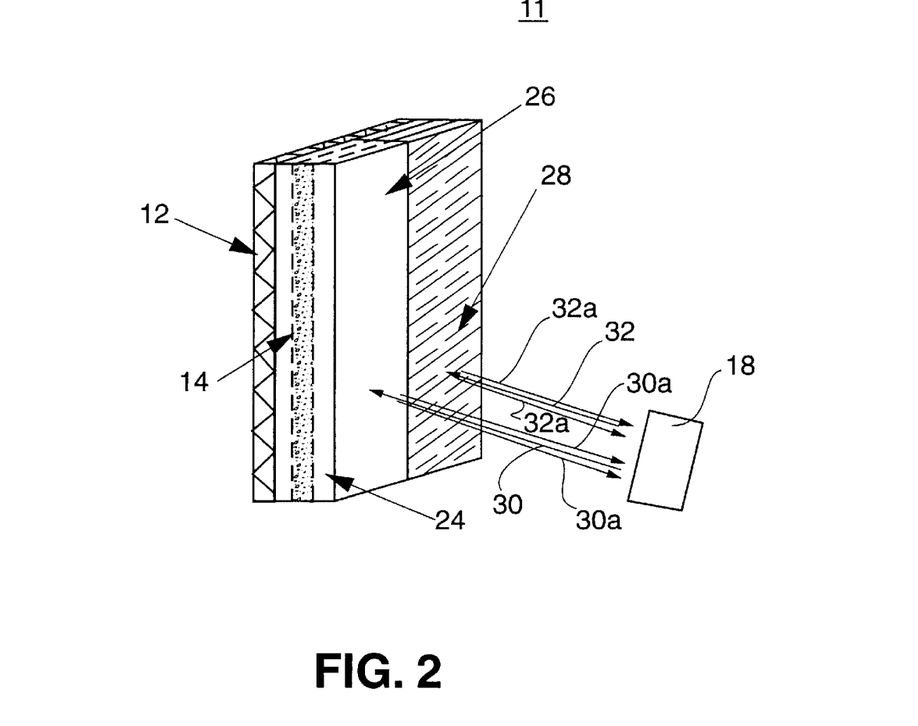
FIG. 2 is a perspective view of a further sensing device made in accordance with the principles of the present invention.

Referring now to FIG. 1, there is shown a sensing device, designated generally at 10, and a related embodiment of the invention is shown in FIG. 2. The component 10 includes a reflective layer 12 that is preferably a retroreflective layer 12 intercoupled to a sensing layer 14 by a coupling layer 16. The sensing layer 14 comprises sensing means having an initial optical absorption capacity and being disposed in a substantially fixed orientation with respect to the retroreflective layer 12 for (i) sensing a presence of the environmental factor, (ii) experiencing a change in optical absorption capacity responsive to said environmental factor, and (iii) transmitting and attenuating light. As such, when an environmental factor (not shown) to be sensed is present, the sensing layer 14 increases in optical absorption capacity, in that it absorbs more of the light which passes through it.

A light source/receiver 18 projects a beam 20 onto the sensing layer 14. The beam 20 is preferably a well-collimated beam. If the environmental factor (not shown) is present, the optical absorption capacity of the sensing layer 14 increases such that the beam 20 is attenuated as it passes through the sensing layer 14. The retroreflective layer 12 reflects the beam 20 back in the form of reflected return beam 22 to the light source/receiver 18 for processing.

Referring now to FIG. 2, a sensing device is designated generally at 11 which differs from the sensor component 10 of FIG. 1 in the addition of a protective, shielding layer 24 which seals off a first portion 26 of the sensing layer 14 from exposure to the environment, leaving a second portion 28 of the sensing layer 14 exposed to the environment. As such, when the environmental factor is present, the first portion 26 of the sensing layer 14 is prevented from experiencing a change in optical absorption capacity responsive to the environmental factor, while the second portion 28 experiences increased optical absorption capacity.

The shielding layer 24 thus operates as a sealing means for sealing off a first portion 26 of the sensing layer 14 from exposure to the environment such that said first portion 26 is prevented from experiencing a change in optical absorption capacity responsive to said environmental factor such that the second portion 28 of the sensing layer 14 remains exposed to said environment.

Figure 2A:
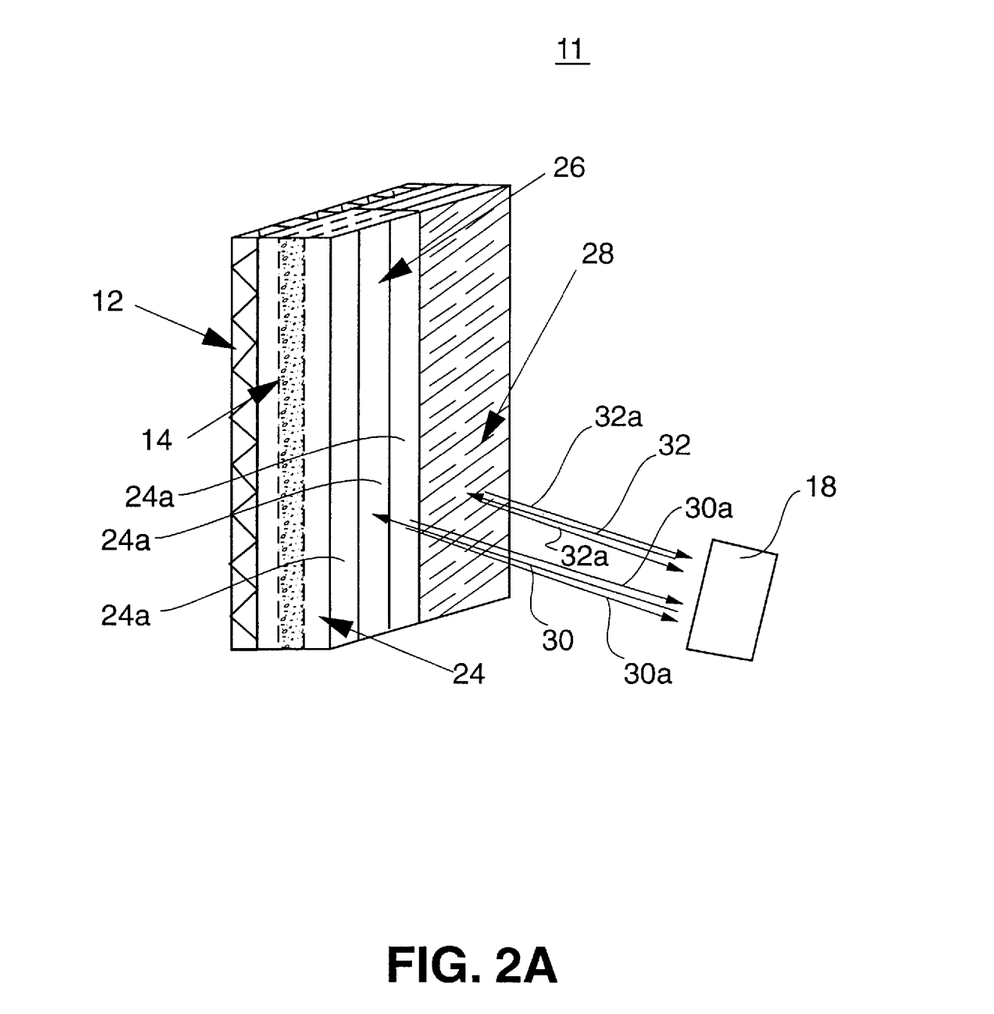
FIG. 2A is a perspective view of an alternative embodiment of the sensing device of FIG. 2.

Referring now to FIG. 2, the shielding layer 24 (sensing means) may alternatively comprise a plurality of separate, individual shield devices 24a. Preferably, at least two of the plurality of separate, individual shield devices 24a each comprise different material properties which experience different rates and extents of natural degradation from exposure to the environment. The phrase "natural degradation" as used herein shall refer broadly to any and all forms of aging, corrosion, erosive action and breakdown. As such, when the individual shields 24a differ in their rates of natural degradation, they provide a spectrum of response to aging and sensing degradation effects to improve the calibration of the device 11.

The invention is completed by projecting at least first and second beams 30 and 32 from light source/receiver 18 onto the sensing device 11 or by scanning a single a single beam across the sensing device 11. The beams 30 and 32 are reflected backwardly as reflected beams 30a and 32a. It is to be understood that a continuous beam of light may be thought of as a single beam or as a plurality of beams, in that the return beams 30a and 32a will each have different intensities even though they originated from the same source (18) at a single intensity.

The shielding layer 24 prevents the presence of environmental factors from contributing to attenuation of the first beam 30, and the first return beam 30a is therefore described as being unattenuated. The light source/receiver 18 includes light-receiving means for receiving the reflected light 30a and 32a reflected from the retroreflective layer 12, and processing means operatively connected to the light-receiving means for measuring an extent of attenuation of the reflected light 32a in comparison with the unattenuated reflected light 30a.

The processing means embodied in light source/receiver 18 preferably comprises means for (i) comparing intensities of the first and second reflected light 30a and 32a and (ii) computing a diagnostic ratio which is proportional to a ratio of said intensities, and (iii) determining from said diagnostic ratio a quantitative presence of the environmental factor which caused the increased optical absorption capacity of the second portion 28 of the sensing layer 14.

The retroreflective layer 12 preferably comprises conventional retroreflective materials which are known to reflectively redirect light from a first direction to a second direction substantially opposite the first direction and thus along a same movement path but opposite in direction. Such retroreflective materials can have several thousand times the equivalent reflectivity of white paper.

The sensing layer 14 is sensitive to the environmental factor as discussed above, and preferably additionally affects light in a manner which is proportional to the concentration or magnitude of the factor. The reflected return beam 32a is thus attenuated by an amount proportional to the factor. The light reflected from the exposed portion 28 of the device 11 will thus be increasingly affected by the presence of the environmental factor to which the sensing layer 14 is sensitive. Accordingly, the light beam 30 will be more strongly reflected from the device 11, whereas the light beam 32 will be less strongly reflected. A light receiving means, preferably incorporated within light source 18, will receive the reflected beams 30a and 32a and compute a ratio of these two beams to indicate the quantitative presence of the factor being measured.

The sensing layer 14 may illustratively comprise a composition of lead acetate and polyvinyl alcohol, but may of course comprise any suitable sensing layer which is sensitive to a desired environmental factor. By dividing the sensing layer 14 into a first portion 26 which is unaffected by the environmental factor being sensed, and another portion 28 which remains exposed to the environmental factor, a self-calibration function is thereby achieved to account for aging and deterioration of the components of the sensing device 11, as will be understood to those having ordinary skill in this field. The first isolated portion 26 comprises one or more regions which are isolated from environmental effect. The exposed portion 28 comprises one or more regions as well, all of which are exposed to one or several environmental factors. The sensing layer 14 might illustratively comprise a sulphur compound sensor. It will thus be appreciated that the sensing device 11 is operable without utilizing an external power source, and is remotely readable at any suitable distance as accomplished by the light source 18.

Figure 3:
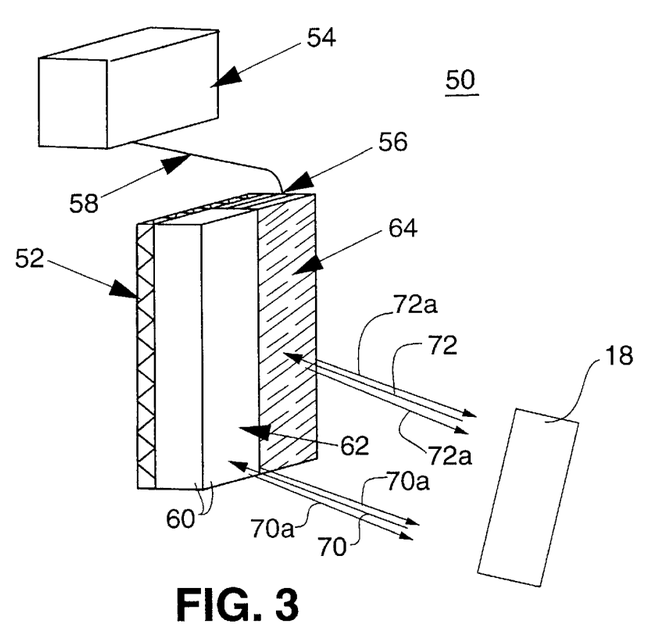
FIG. 3 is a perspective view of another alternative embodiment of the sensing device of FIG. 2.

Referring now to FIG. 3, there is shown another embodiment of the invention, in the form of a sensing device designated generally at 50. A reflective layer 52 preferably comprises a retroreflective material. A sensing module 54 comprises means for (i) sensing a presence of an environmental factor, and (ii) producing an electrical signal responsive to said environmental factor, in any suitable manner. The electrical signal is preferably proportional to an environmental factor to be sensed.

A light-modulating means 56 is electrically connected by an electrical or electronic link 58 to the sensing module 54 for (i) receiving the electrical signal produced by the sensing module 54, (ii) experiencing a change in optical absorption capacity responsive to said electrical signal, and (iii) transmitting and attenuating light. The light-modulating means 56 might illustratively comprise a liquid crystal electronic display. A protective, shielding layer 60, similarly to the shielding layer 24 of FIG. 2, seals off a first portion 62 of the light-modulating means 56 from exposure to the environment, leaving a second portion 64 of the light-modulating means 56 exposed to the environment.

The light-modulating means 56 comprises an electro optic material to operate as a photoactive sensing layer. Such material effects light in a manner proportional to an applied electrical current transmitted through the link 58, such as liquid crystal devices (LCD) as are widely used in electronic displays. Therefore, the embodiment of the sensing device 50 in FIG. 3 provides substantially the same result as the sensing device 11 in FIG. 2 in that the amount of reflected light varies proportionally to the intensity of the environmental factor being sensed, although this result is accomplished by different means in the sensing device 50.

The further concepts of the present invention include a preferred method of sensing an environmental factor, said method comprising the steps of:

(a) exposing to the environmental factor a sensing means 14 having an initial optical absorption capacity for (i) sensing a presence of the environmental factor, (ii)

experiencing a change in optical absorption capacity responsive to said environmental factor, and (iii) transmitting and attenuating light 30 and 32;

(b) directing light 30 and 32 through the sensing means 14;

(c) reflecting the light which has passed through the sensing means 14 to a light-receiving means (embodied within source/receiver 18) for processing.

Figure 4:
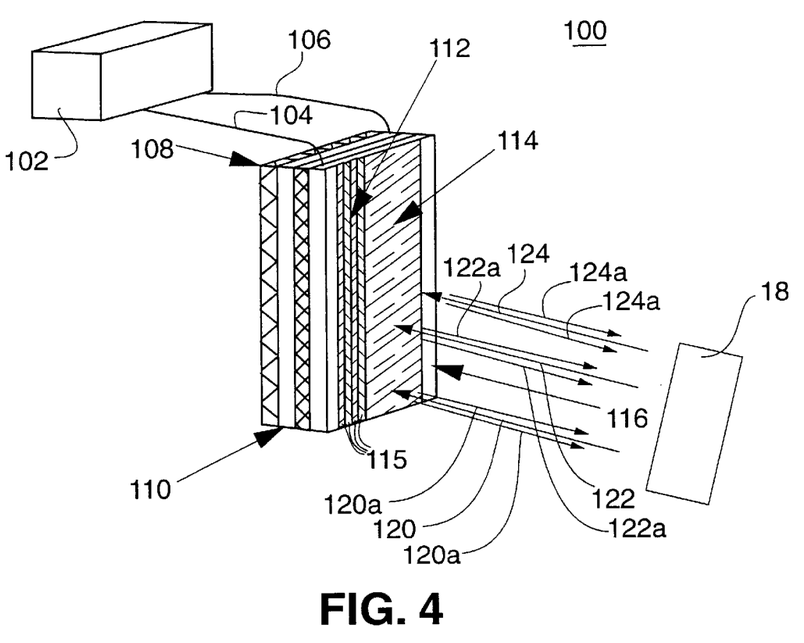
FIG. 4 is a perspective view of still another alternative embodiment of the sensing device of FIG. 2.
Figure 5:
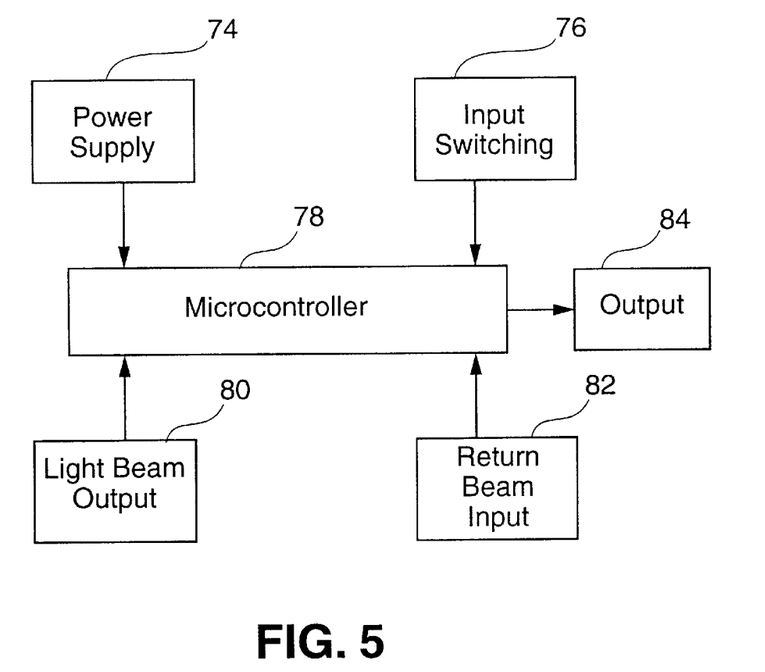
FIG. 5 and FIG. 6 are schematic block diagrams of a control circuitry of the sensing device.

Referring now to FIG. 5, there is shown a schematic block diagram of the control circuitry used in operating the light source/receiver 18 of FIGS. 1–4. The components represented in FIG. 5 are readily understandable to those of ordinary skill in the field of conventional circuitry control operations, and represent only one of several circuit arrangements which might be used to implement the present invention. Therefore, any suitable control circuitry arrangement which could be employed to provide the functions described herein are within the scope of the present invention.

More specifically, a power source 74 and input switching 76 are operatively connected to microcontroller 78, which is operatively connected to light beam output 80, return beam input 82, and output 84. Output 84 is preferably a visual out display but may alternatively comprise any suitable output device, including a device for further processing or storing data. The operative connections preferably comprise electronic connections. When it is desired to emit a light beam from the light source/receiver 18, the input switching 76 is actuated in any manner known to those skilled in the art to cause microcontroller 78 to actuate the light beam output 80, causing the input beams discussed above in connection with FIGS. 1–4.

The return beams (such as beams 22 of FIG. 1, beams 30a and 32a of FIG. 2, and so forth), are received by the return beam input 82 which assigns a value to the beams, preferably based on their intensity. The return beam 82 thereafter produces an electronic signal corresponding to the beam intensity, and communicates that signal to the microcontroller 78 which processes the signal and produces corresponding output signals to the visual output display 84. In this manner, the functions described above of producing and receiving light beams, and processing the return beams as indicators of the altered optical opacity of the sensing layer 14 to thereby determine the presence and magnitude of an environmental factor being sensed, are accomplished by the control circuitry represented in FIG. 5.

The block layout design of FIG. 5 illustrates the conventional nature of the hardware necessary to render the light source/receiver 18, and the various output, receiving and processing functions associated therewith, operative. Those having ordinary skill in the field know to program the microcontroller 78 in various conventional ways to create these described functions. The operation sequences described herein, and as explained in connection with the control circuitry of FIG. 5, are readily ascertainable to those of ordinary skill.

Figure 6:
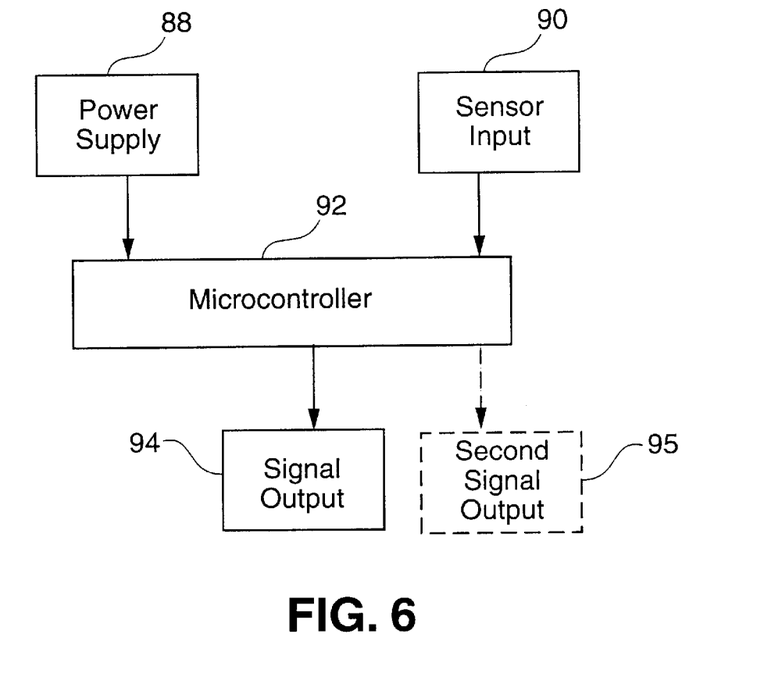

Referring now to FIG. 6, there is shown a schematic block diagram of the control circuitry used in operating the sensing module 54 of FIG. 3. The components represented in FIG. 6 are readily understandable to those of ordinary skill in the field of conventional circuitry control operations. A power supply 88 and a sensor input 90 are operatively connected to microcontroller 92, which is operatively connected to a signal output 94. The signal output 94 is then electronically coupled to the link 58 of the sensing device 50 in FIG. 3. As is readily apparent to those of ordinary skill in the field, the sensor input 90 operates in any conventional manner for sensing an environmental factor, and transmits the information it senses to the microcontroller 92, which actuates the signal output 94 to transmit an electrical signal through the link 58 (FIG. 3) to the light-modulating means 56 (FIG. 3).

The block layout design of FIG. 6 illustrates the conventional nature of the hardware necessary to render the sensing device 50, and more specifically the sensor module 54, operative. Those having ordinary skill in the field can program the microcontroller 92 in various conventional ways for processing the input from the sensor input and transmitting this information in the form of an electrical signal via the signal output 94.

Referring now to FIG. 4, there is shown yet another embodiment of a sensing device designated generally at 100. The sensing device 100 includes a sensing module 102 electrically connected by electrical or electronic links 104 and 106 to an output apparatus comprising a reflective layer 108 that is preferably a retroreflective layer intercoupled to a light-modulating layer 110. The light-modulating layer 110 includes a plurality of separate light-modulating means 112 each for (i) receiving an electrical control signal, (ii) experiencing a change in optical absorption capacity responsive to said electrical control signal, and (iii) transmitting and attenuating light.

The light-modulating layer 110 further includes a sensor-output section 114, a portion of which might be covered by a protective shield 116. The sensing module 102 is a control module which is capable of different functions. One function of the module 102 would be to produce a plurality of electrical control signals and transmit them to the plurality of light-modulating means 112 to thereby alter the optical absorption capacity of at least some of the light modulating means 112, such that some of said light-modulating means comprise a plurality of different optical absorption capacities. The control of the various light-modulating means 112 would be accomplished through the link 104 in such a manner that different voltages would be applied to the different light-modulating means 112 so as to vary each of their light absorption capacities to different degrees.

The module 102 may optionally further comprise a sensing means for (i) sensing a presence of an environmental factor (ii) producing an electrical signal responsive to said environmental factor, and (iii) transmitting said signal to the sensor output section 114 of the device to thereby alter the optical absorption capacity of said sensor-output section 114. In this manner, the control circuitry for the sensing device 100 would be equivalent to the circuitry depicted schematically in FIG. 6, with the addition of a second signal output 95 shown in phantom line in FIG. 6. The second signal output 95 would operate to transmit signals responsive to the presence and/or magnitude of an environmental factor through the electronic link 106 so that it reaches the sensor-output section 114.

It will be understood to those of ordinary skill in the field from the above description that the sensing device 100 comprises a combination of digital output (in the form of a plurality of light-modulating means 112) and analog output (in the form of the sensor-output section 114). Information is read from the light-modulating means 112 and the sensor-output portion 114 remotely by the light source/receiver 18 in the same manner described above in conjunction with FIGS. 1–3. One of many possible applications would be to have a plurality of the sensing devices 100 in various locations, and there would thus be the need to categorize and keep track of all of the various sensing devices 100 and the different information each would display. The plurality of light-modulating means 112 on each sensing device 100 could be used simply to provide an identifying code, and the sensor-output portion 114 would then provide the substantive information relating to the presence and/or magnitude of an environmental factor being sensed.

In this manner, one or more light source/receivers 18 would project light 120 onto the various light-modulating pluralities 112 of each sensing device 100 to determine from the return light 120a which device is being read, and the light source 18 would correspondingly project another light beam 122 onto the sensor-output portion 114 to determine from the reflective return light 122a the presence and/or magnitude of an environmental factor being sensed. The readout could also be accomplished by a multiplexer arrangement, as known to those having ordinary skill in the field, such that two or more sensors could be multiplexed to a single retroreflective output device which would display in turn the identification number of each sensor along with its output level.

A portion 116 of the sensor-output section 114 may be sealed off from communication with the module 102, such as by being unconnected thereto, thereby permitting light source 118 to project additional light beams 124 onto the unaffected portion 116 for use as a comparison/calibrating function in the same manner described above in conjunction with sealed portion 24 (FIG. 2) and sealed portion 60 (FIG. 3).

Referring still to FIG. 4, the further alternative would be to rely on the plurality of light-modulating means 112 for more than mere identification, perhaps by altering the respective light absorption capacities such that they would be collectively readable via the return light 120a to identify the presence and/or magnitude of an environmental factor. In this manner, a sensing device could be constructed without the need for the sensor-output section 114, and the module 102 would comprise a sensing means for (i) sensing a presence of the environmental factor, (ii) producing an electrical signal responsive to a presence of said environmental factor, and (iii) transmitting said signal as an input signal from the microprocessing means (i.e. 92 of FIG. 6) to thereby cause said microprocessing means to produce a plurality of electrical control signals to alter the optical absorption capacities of at least some of the plurality of light-modulating means 112 in accordance with an identifying pattern of different optical absorption capacities responsive to said input signal, such that said pattern corresponds to and identifies the presence of said environmental factor.

From the above descriptions, those having ordinary skill in the field will understand that the present invention operates on many different levels, including the following: (i) a sensing device which is entirely analog in function (FIGS. 1–2), and (ii) a sensing device having a combination of both analog and digital functions (FIG. 4), and (iii) a sensing device which operates entirely in digital function (the description of the encoding in conjunction with portion 112 of FIG. 4). In this latter case, the beam 120 would simply be swept across the various strips 115 of the plurality of light-modulating means 112, such that a plurality of various return beams 120a would be received by the light source/receiver 18, which would vary in intensity based on the code of varying light absorption capacities of the different strips 115 in accordance with a predetermined code which would identify the presence and/or magnitude of an environmental factor. Or multiplexing readout could be used.

Referring still to FIG. 4, it will be appreciated that by the use of appropriate external polarizers applied to the plurality of light-modulating means 112, an optical density may be produced by the combination of polarizer and an electro-optic device such as a liquid crystal (assuming the means 112 comprises an electro-optic device in this case) so as to be adjustable over a very wide range. A user would still read out information from the means 112 remotely by light beam 120 using the retroreflective principle provided by retroreflective layer 108 to simplify the process. The advantage of this kind of digital readout, which is a byproduct of the contiguous strips 115 of the LCD light-modulating means 112, is that less noise is produced and a higher degree of readout resolution possibilities is possible because an extensive matrix of coding possibilities are provided. The higher the number of strips 115 there are, the higher matrix degree of possibility there will be for a number of different codes.

It is also to be understood that the scope of the present invention includes the capacity of the module 102 to independently transmit data to the electro-optic devices mentioned above as being embodied as items 112. That data can then be converted to an image which can be read out using the retroreflective layer 108.

A further embodiment may be described in conjunction with FIGS. 1–2. Those having ordinary skill in the field will appreciate that the sensing layer 14, instead of comprising material having variable optical absorption capacity, might instead having variable optical light-scattering capacity. The same alternative may apply with respect to the light-modulating means 56 of FIG. 3, and the light-modulating layer 110 of FIG. 4. Further, any material which is capable of transmitting light in selectively variable degrees is within the scope of the present invention. Materials having variable optical opacity, optical light absorption capacity, and optical light-scattering capacity are within the scope of the invention, as is any other type of material having any adjustable capacity to transmit light therethrough.

It is to be understood that the inventive combinations described herein are applicable to a wide variety of uses. The phrase "transmit" as used herein shall be broadly construed to include the concept of an object which can receive light or heat and have said light or heat pass through it. For example, a plate of glass which permits light to pass through it is transmitting the light as the term "transmit" is intended herein, even though the glass is not producing the light.

It is also to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

We claim:

1. A sensing device for sensing an environmental factor, said device comprising:

reflective means for reflecting light;

sensing means having an initial optical absorption capacity and being disposed in a substantially fixed orientation with respect to the reflective means for (i) sensing a presence of the environmental factor, (ii) experiencing a change in optical absorption capacity responsive to said environmental factor, and (iii) transmitting and attenuating light;

wherein said reflective means is disposed in a facing alignment with respect to the sensing means such that light which is caused to pass through said sensing means is reflected by said reflective material;

wherein the reflective means comprises retroreflective means for reflectively redirecting light from a first direction to a second direction substantially opposite the first direction and thus along a same movement path but opposite in direction.

2. The sensing device as defined in claim 1, wherein the sensing means is operable as defined in claim 1 without utilizing an external power source.

3. The sensing device as defined in claim 1, wherein the reflective means comprises a layer of retroreflective material and the sensing means comprises a layer of environmentally-sensitive material which is chemically reactable with the environmental factor, said retroreflective layer and said sensing layer being disposed in a parallel, facing relationship, said device further comprising:

sealing means for sealing off at least a portion of the sensing layer from exposure to a surrounding environment such that said portion is prevented from experiencing a change in optical absorption capacity responsive to said environmental factor.

4. A sensing device for sensing an environmental factor, said device comprising:

reflective means for reflecting light;

sensing means having an initial optical light-scattering capacity and being disposed in a substantially fixed orientation with respect to the reflective means for (i) sensing a presence of the environmental factor, (ii) experiencing a change in optical light-scattering capacity responsive to said environmental factor, and (iii) transmitting and attenuating light;

wherein said reflective means is disposed in a facing alignment with respect to the sensing means such that light which is caused to pass through said sensing means is reflected by said reflective material.

5. A sensing device for sensing an environmental factor, said device comprising:

sensing means having an initial optical absorption capacity for (i) sensing a presence of the environmental factor, (ii) experiencing a change in optical absorption capacity responsive to said environmental factor, and (iii) transmitting and attenuating light; and reflective means disposed in a substantially fixed orientation with respect to the sensing means for reflecting light which passes through the sensing means;

sealing means for sealing off a first portion of the sensing layer from exposure to a surrounding environment such that said first portion is prevented from experiencing a change in optical absorption capacity responsive to said environmental factor such that a second portion of the sensing layer remains exposed to said environment.

6. The sensing device of claim 5, wherein the sealing means comprises a plurality of separate, individual shield devices.

7. The sensing device of claim 6, wherein at least two of the plurality of separate, individual shield devices each comprise different material properties which experience different rates of natural degradation from exposure to the surrounding environment.

8. The sensing device of claim 5, further comprising:

a light source means for directing light onto the sensing means; and a light-receiving means for receiving light reflected from the reflective means.

9. The sensing device of claim 8, further comprising:

processing means operatively connected to the light-receiving means for measuring an extent of attenuation of the light reflected from the reflective means.

10. A sensing device for sensing an environmental factor, said sensing device comprising:

sensing means having an initial optical absorption capacity for (i) sensing a presence of the environmental factor, (ii) experiencing a change in optical absorption capacity responsive to said environmental factor, and (iii) transmitting and attenuating light; and reflective means disposed in a substantially fixed orientation with respect to the sensing means for reflecting light which passes through the sensing means;

sealing means for sealing off a first portion of the sensing layer from exposure to a surrounding environment such that said first portion is prevented from experiencing a change in optical absorption capacity responsive to said environmental factor such that a second portion of the sensing layer remains exposed to said environment;

a light source means for directing light onto the sensing means; and a light-receiving means for receiving light reflected from the reflective means;

wherein the light source means further comprises means for directing first and second beams of light onto the first and second portions of the sensing means, respectively, said device further comprising:

processing means operatively connected to the light-receiving means for (i) comparing intensities of the first and second beams after they are reflected by the reflective means and (ii) computing a diagnostic ratio which is proportional to a ratio of said intensities, and (iii) determining from said diagnostic ratio a quantitative presence of the environmental factor.

11. A sensing device for sensing an environmental factor, said sensing device comprising:

sensing means having an initial optical absorption capacity for (i) sensing a presence of the environmental factor, (ii) experiencing a change in optical absorption capacity responsive to said environmental factor, and (iii) transmitting and attenuating light; and reflective means disposed in a substantially fixed orientation with respect to the sensing means for reflecting light which passes through the sensing means;

sealing means for sealing off a first portion of the sensing layer from exposure to a surrounding environment such that said first portion is prevented from experiencing a change in optical absorption capacity responsive to said environmental factor such that a second portion of the sensing layer remains exposed to said environment;

a light source means for directing light onto the sensing means; and a light-receiving means for receiving light reflected from the reflective means;

wherein the light source means further comprises means for directing a beam of light onto the first and second portions of the sensing means and causing the reflective means to reflect said beam back through said first and second portion of said sensing means in the form of first and second return beams, respectively, said device further comprising:

processing means operatively connected to the light-receiving means for (i) comparing intensities of the first and second return beams after they are reflected by the reflective means and (ii) computing a diagnostic ratio which is proportional to a ratio of said intensities, and (iii) determining from said diagnostic ratio a quantitative presence of the environmental factor.

12. A method of sensing an environmental factor, said method comprising the steps of:
   (a) exposing to the environmental factor a sensing means having an initial optical absorption capacity for (i) sensing a presence of the environmental factor, (ii) experiencing a change in optical absorption capacity responsive to said environmental factor, and (iii) transmitting and attenuating light;
   (b) directing light through the sensing means from a light source disposed in a remote location with respect to the sensing means and without structural attachment to said sensing means; and
   (c) reflecting the light which has passed through the sensing means to a light-receiving means for processing.

* * * * *